(12) United States Patent
Popescu

(10) Patent No.: US 6,501,828 B1
(45) Date of Patent: Dec. 31, 2002

(54) METHOD AND APPARATUS FOR INFLUENCING X-RAYS IN A BEAM PATH

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 42 days.

(21) Appl. No.: 09/692,231

(22) Filed: Oct. 20, 2000

(30) Foreign Application Priority Data

Oct. 21, 1999 (DE) .......................................... 199 50 794

(51) Int. Cl.[7] ................................................ G21K 1/04
(52) U.S. Cl. ...................... 378/150; 378/151; 378/152; 378/153; 378/145; 378/158
(58) Field of Search ................................. 378/151, 152, 378/65, 147, 197, 205, 98.8, 11, 150, 153, 145, 158; 250/505.1

(56) References Cited

U.S. PATENT DOCUMENTS

| | | | | |
|---|---|---|---|---|
| 4,672,212 A | * | 6/1987 | Brahme | 250/505.1 |
| 4,868,843 A | * | 9/1989 | Nunan | 250/505.1 |
| 5,377,252 A | | 12/1994 | Liebetruth | |
| 5,818,902 A | * | 10/1998 | Yu | 378/151 |
| 6,196,715 B1 | * | 3/2001 | Nambu et al. | 378/11 |

FOREIGN PATENT DOCUMENTS

| | | |
|---|---|---|
| DE | OS 41 37 242 | 6/1993 |
| DE | OS 197 55 764 | 6/1999 |

* cited by examiner

Primary Examiner—Robert H. Kim
Assistant Examiner—George Wang
(74) Attorney, Agent, or Firm—Schiff Hardin & Waite

(57) ABSTRACT

An x-ray apparatus has an x-ray source and an x-ray receiver, the x-ray source being adjustable relative to a subject and emitting x-rays in the direction toward the x-ray receiver during the course of radiological exposures of the subject. The x-ray apparatus has an arrangement in the beam path of the x-rays for influencing the shape and/or the intensity profile of the x-ray beam, and this arrangement is dynamically adjustable during radiological exposures of the subject for influencing the shape and/or the intensity profile of the x-rays.

14 Claims, 2 Drawing Sheets

METHOD AND APPARATUS FOR INFLUENCING X-RAYS IN A BEAM PATH

BACKGROUND OF THE INVENTION

1. Field of the Invention

The present invention is directed to an x-ray apparatus of the type having an x-ray source and an x-ray receiver, the x-ray source being adjustable relative to a subject and emitting x-rays in a direction toward the x-ray receiver during the course of radiological exposures of the subject, and having an arrangement in the beam path of the x-rays for influencing the shape and/or the intensity profile of the x-ray. The invention is also directed to a method for influencing x-rays in the beam path.

2. Description of the Prior Art

When producing x-ray images of a subject, there is a basic desire to present the region of the subject of interest for the examination with very good quality in the x-ray image, i.e. with little image noise. The subject under examination is therefore charged with such an x-ray dose that a good signal-to-noise ratio is established, i.e. the image noise is relatively low in the image region representing the region of interest. Particularly in the medical application of x-rays, for example the production of x-ray images of relatively small tissue regions of diagnostic interest such as the heart or vessels, it is disadvantageous that the tissue that surrounds the tissue of interest and is diagnostically less relevant or irrelevant and the presentation of which with poorer quality could be tolerated is likewise exposed to the high x-ray dose in the image registration.

In order to reduce the radiation stress for the tissue surrounding the tissue of interest, for example, it is known from computed tomography to employ wedge filters that usually influence an x-ray beam emanating from an x-ray source such that the intensity of the x-rays of the x-ray beam incident on the central x-ray detectors of the x-ray receiver is higher than the intensity of the x-rays that strike the outer x-ray detectors of the x-ray receiver, since these x-rays are already attenuated by the wedge filter before passing through the subject. When, accordingly, the tissue of interest of a subject under examination is placed in the rotational center of the computed tomography apparatus, a comparatively low radiation stress occurs for the tissue surrounding the tissue of interest as a result of the effect of the wedge filter. The wedge filters employed are usually adapted to the absorption profile of a homogeneous, circular phantom. The intensity profile of the x-rays that can be generated with such a wedge filter, accordingly, is relatively well-adapted to the absorption profile of the phantom, but is only well-adapted to the absorption profile of different body slices of a patient or different patients in exceptional cases.

Another procedure for reducing the radiation stress on the tissue surrounding the tissue of interest is to employ a collimator allocated to the x-ray source having a central radiation window that is smaller in size, so that, for example given x-ray imaging with a computed tomography apparatus, the tissue of interest is imaged in a circular slice whose center coincides with the rotational center of the computed tomography apparatus. This procedure, however, allows only the diameter of the circular slice exhibiting the tissue of interest to be set, and also requires that the tissue of interest in an examination be placed as exactly as possible in the rotational center of the x-ray system.

SUMMARY OF THE INVENTION

An object of the present invention is to provide an x-ray system of the type initially described wherein the generation of a qualitatively high-grade x-ray image of a region of interest of a subject is simplified and involves less radiation stress for the region surrounding the region of interest of the subject. It is also based on an object of the present invention to provide a method for reducing the radiation stress in imaging with x-rays for a region surrounding a region of interest in a subject.

The object is inventively achieved by an x-ray apparatus having an x-ray source and an x-ray receiver, the x-ray source being adjustable relative to a subject and emitting x-rays in the direction toward the x-ray receiver during the course of radiological exposures of the subject, and having an arrangement in the beam path of the x-rays for influencing the shape and/or the intensity profile of the x-ray, wherein the arrangement can be dynamically set for influencing the shape and/or the intensity profile of the x-rays during radiological exposures of the subject. Such dynamic, i.e. automatically variable, setting of the arrangement allows the shape and/or the intensity profile of the x-rays emanating from the x-ray source in the direction of the subject to be readily adapted in the context various, successive radiological exposures of the subject, for example due to adjustments of the x-ray source relative to the subject under examination which result in different positions of the focus of the x-ray source relative to a region of interest in the subject, so that the region of the subject surrounding the region of interest is charged with no radiation or with only slight x-radiation. Given a rotational adjustment of the x-ray source relative to the subject, the region of interest thereby need not necessarily be located in the rotational center of the x-ray source, so that the image registration is in turn simplified due to the elimination of tedious alignment processes of the subject and of the x-ray system relative to one another. The adjustments of the arrangement for influencing the shape and/or the intensity profile of the x-radiation dependent on the respective conditions for different radiological exposures of a subject preferably ensues by a control unit allocated to the arrangement.

In an embodiment of the invention the arrangement for influencing the shape and/or the intensity profile of the x-rays is a collimator allocated to the x-ray source and exhibiting a radiation window, with the size of the radiation window being dynamically adjustable. In a version of this embodiment, the size of the radiation window of the collimator can be varied by elements of the collimator that are movable relative to one another. By an appropriate adjustment of the elements, accordingly, not only the shape of the x-ray beam, i.e. its beam cross-section, but also the position of the radiation window of the collimator can be set relative to the focus of the x-ray source, and thus relative to the path of the x-rays. In this way, the path of the x-rays can be influenced such that, independently of the position of the focus relative to a subject under examination, essentially only the region of interest of the subject is transirradiated. The x-rays that strike the material of the collimator are significantly attenuated in comparison the x-rays passing through the radiation window of the collimator that can be dynamically adjusted in terms of its size, shape and position, are even completely absorbed by the material of the collimator, so that the x-ray dose with which the region of a subject surrounding a region of interest is charged is significantly lower than the x-ray dose that charges the region of interest.

In a version of the this embodiment that the elements of the collimator move along a circular path whose center of curvature preferably lies in the focus of the x-ray source. This version is advantageous because, given a constant thickness of the material of the adjustable elements of the collimator, the possibilities of variation arising from the adjustment of the elements in the absorption profile of the collimator are minimized since the x-rays travel essentially the same distance when traversing the elements. By providing elements that are nearly circularly curved to emulate the curvature of the circular path, this allows, for selected settings of the elements of the collimator and intensities of the x-rays, determination and storage of only a few absorption profiles of the collimator required for the imaging. These profiles need only be subjected to simple shift operations for changing (adjusting) the absorption profile of the collimator corresponding to the actual setting of the elements given an x-ray exposure. Planar or differently shaped elements can be employed instead of circularly curved elements, but these should be moved along the circular path given settings of the elements modifying the size of the radiation window for minimizing the variation possibilities in the absorption profile of the collimator. Otherwise, the absorption profiles of the collimator vary greatly given different settings of the elements, since the path length of the x-rays through the collimator material or the adjustable elements thereof is a function of the distance of the elements from the focus of the x-ray source. In this case, respective absorption tables must be produced for various settings of the elements, since the absorption profiles required for the reconstruction of x-ray images cannot be determined with simple shift operations of a few, identified absorption profiles.

In an embodiment of the invention the arrangement for influencing the shape and/or the intensity profile of the x-rays include at least one wedge filter allocated to the x-ray source and having elements that are movable relative to one another, these elements in one version of the invention moving on a circular path like the elements of the collimator for minimizing the variation possibilities in the absorption profile of the wedge filter. The shape and/or the intensity profile of the x-rays emanating from the x-ray source also can be influenced with the adjustable elements of the wedge filter so that a diagnostically less relevant region surrounding a region of diagnostic interest is charged with a comparatively low x-ray dose.

A further embodiment of the invention has a measuring arrangement for acquiring the setting of the arrangement for influencing the shape and/or the intensity profile of the x-rays. In another embodiment of the invention, the arrangement for influencing the shape and/or the intensity profile of the x-rays can effect a significant, detectable boost in the intensity profile of the x-rays. In a version of this embodiment, the significant detectable change in the intensity profile of the x-rays is produced by thinning the material and/or thickening the material of arrangement for influencing the shape and/or the intensity profile of the x-rays. Such a thinning of material can, for example, be in the form of a slot, and the thickening of material can be in the form of a ridge. The measuring arrangement as well as the structure that effects the detectable change in the intensity profile serve the purpose—in every x-ray exposure for the current setting of the arrangement for influencing the shape and/or the intensity profile of the x-radiation—of determining the absorption profile that is required for the reconstruction of images from the absorption tables that have been (preferably) determined preceding subject measurements and have been stored.

The inventive method for influencing the shape and/or the intensity profile of the x-ray beam with an inventively fashioned x-ray apparatus includes setting of the beam influencing arrangement on the basis of a function determined before a subject measurement (exposure) dependent on the positions to be assumed by the x-ray source during the subject measurement. The setting of the arrangement preferably ensues with a control that sets the arrangement for influencing the shape and/or the intensity profile during the subject measurement according to the function determined offline, i.e. before a subject measurement. For a computed tomography apparatus, the setting of the arrangement and thus the modulation of the x-rays is, for example, a function of the rotational angle of the x-ray source around the rotational center of the computed tomography apparatus.

The object of the invention is also achieved in a method for influencing the shape and/or the intensity profile of the x-rays of an inventively fashioned x-ray apparatus, wherein the influencing of the shape and/or of the intensity profile of the x-rays ensues on the basis of radiation attenuation values determined during a subject measurement, i.e. online. In this case, the radiation attenuation values determined with a data measuring system are made available to the control unit that calculates and initiates the setting of the arrangement for influencing the shape and/or the intensity profile on the basis of the radiation attenuation values.

DESCRIPTION OF THE PREFERRED EMBODIMENTS

Figure 1:
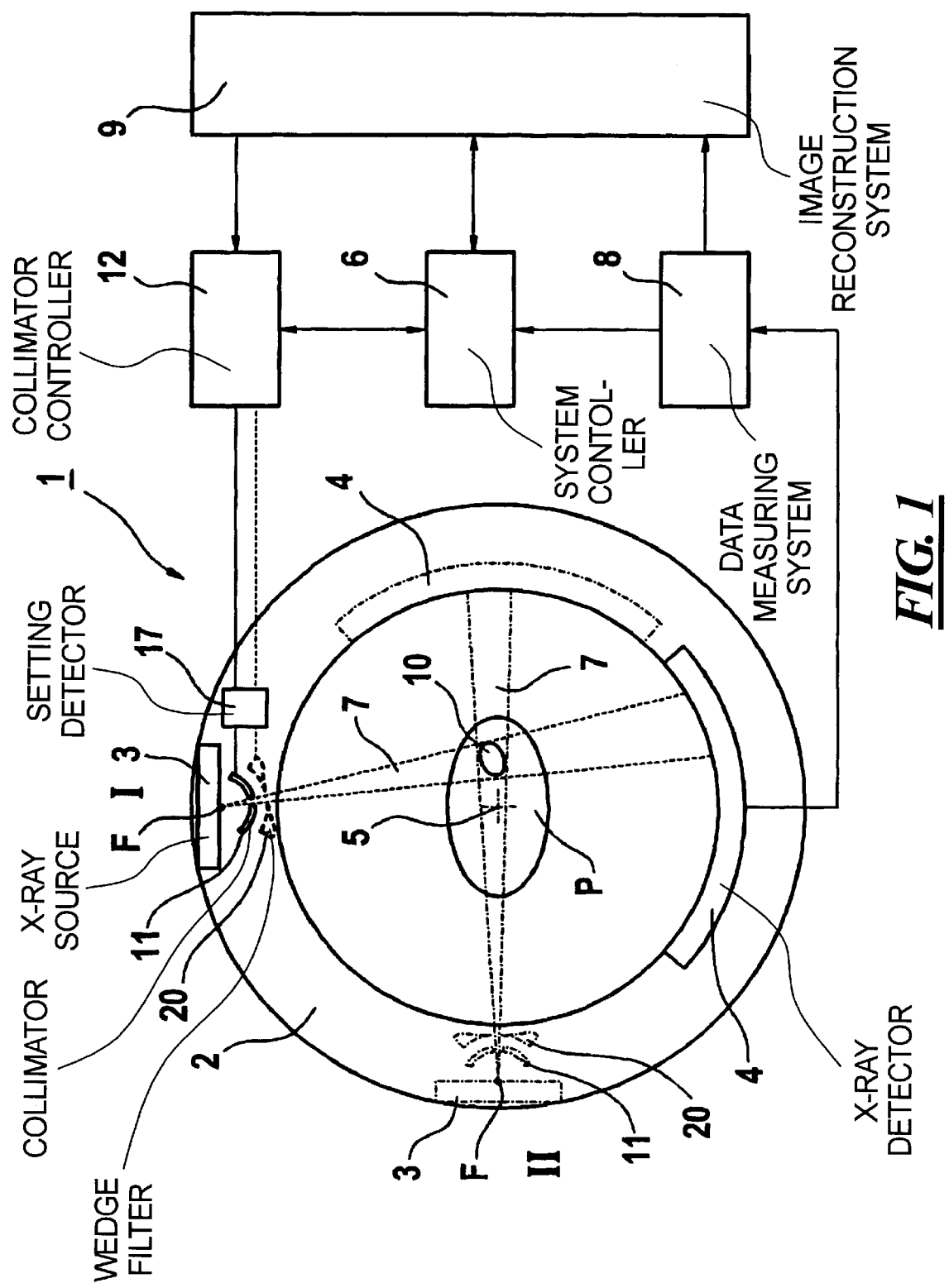
FIG. 1 shows an inventive x-ray apparatus in the exemplary embodiment of a computed tomography apparatus.

FIG. 1 schematically shows an inventive x-ray apparatus in the form of a computed tomography apparatus 1. The computed tomography apparatus 1 has a gantry 2 that is provided with an x-ray source 3 and an x-ray detector 4 and that is rotatable around a rotational center 5. The rotational movement of the gantry 2 is accomplished by an electric drive (in a way not shown) that is driven by a system controller 6 of the computed tomography apparatus 1.

During operation of the computed tomography apparatus 1, the gantry 2 rotates around an examination subject, a patient P in the exemplary embodiment, while a fan-shaped x-ray beam 7 emanates from the x-ray source 3, which penetrates the patient P and is incident on the x-ray detector 4. A data measuring system 8 is connected to the x-ray detector 4, which reads out the radiation attenuation values measured by the x-ray detector 4 during the patient measurement (exposure) and forwards these to an image reconstruction system 9. On the basis of the measured radiation attenuation values and the position data of the gantry 2 that the system controller 6 makes available to the image reconstruction system 9, the image reconstruction system 9 can reconstruct tomograms or 3D images of examined body regions of the patient P in a known manner. The presentation of the reconstructed images can ensue in a known way on a display means that is not shown.

In the exemplary embodiment, the heart 10 of the patient P is diagnostically examined with the computed tomography apparatus 1. The x-ray beam 7 penetrates a slice-shaped cross-sectional volume of the patient P in an x-ray projection and is—in the exemplary embodiment—dynamically influenced by a collimator 11 that is allocated to x-ray source 3 and which has a radiation window 15 that is adjustable in size, shape and position relative to the focus F of the x-ray source 3. This adjustment is made such that the x-ray beam 7 penetrates essentially only the body region of the patient P containing the heart 10, independently of the position of the focus F relative to the patient P. A collimator control 12 allocated to the collimator 11 causes, during operation of the computed tomography apparatus 1, the size, shape and position of the radiation window 15 of the collimator 11 always to be dynamically adapted to the region to be radiologically examined, i.e. it causes the x-ray beam 7 to be shaped so that it penetrates only the body region of the patient P containing the heart 10. This achieves the result that the x-ray dose with which the diagnostically uninteresting tissue surrounding the heart 10 is charged during the radiological examination of the heart 10 is significantly reduced in comparison to known exposure methods. In FIG. 1, the curve of the x-ray beam 7 is shown as an example for two positions I and II of the gantry 2.

Figure 2:
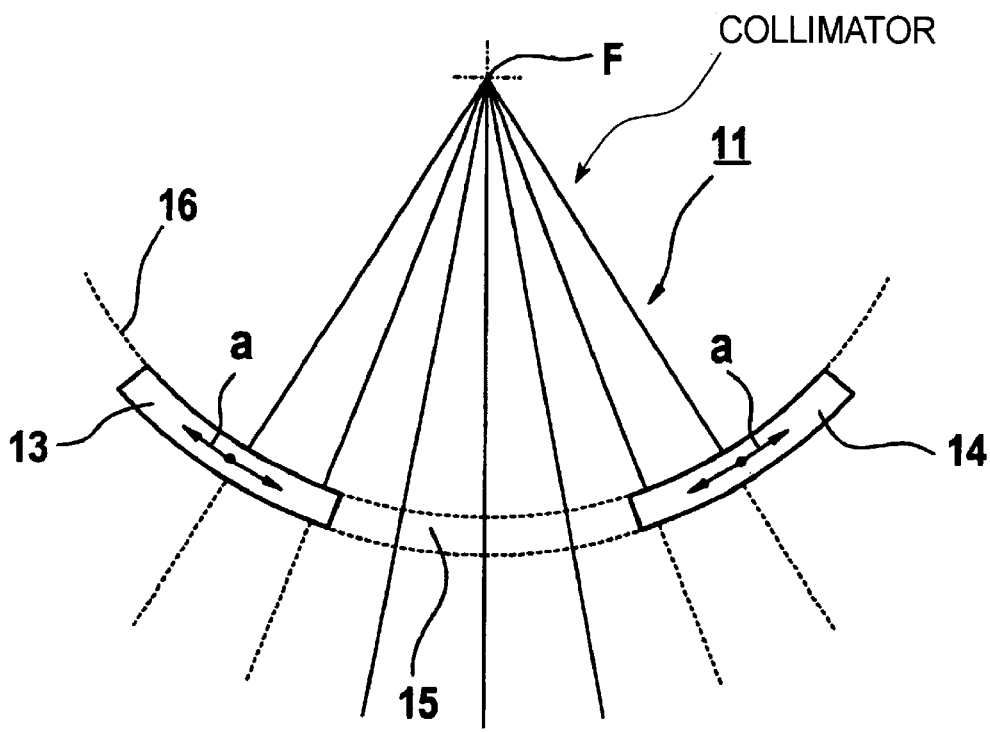
FIG. 2 shows the embodiment of a collimator for the computed tomography apparatus of FIG. 1.

FIG. 2 schematically shows the collimator 11 with elements 13, 14 that can be adjusted in the direction of the double arrows a and that set the size, shape and position of the radiation window 15 relative to the focus F. The elements 13, 14 are drivable independently of one another by the collimator control 12, i.e. they are dynamically adjustable into specific position. Dependent on the material and on the thickness of the material of the collimator 11, only low-intensity x-radiation can proceed to the patient P outside the adjustable radiation window 15. The collimator 11, however, can be fashioned such that the x-rays that strike the elements 13, 14 of the collimator 11 are completely absorbed.

The adjustment of the elements 13, 14 preferably ensues along a circular path 16 whose curvature center lies in the focus F of the x-ray source 3. In this way, possible variations in the absorption profile of the collimator 11 arising due to the adjustment of the elements 13, 14 are reduced, given an essentially constant thickness of the adjustable elements 13, 14 of the collimator 11. This is because the x-rays will always travel a substantially identical distance upon traversal of the elements 13, 14. Knowledge of this absorption profile is required for the reconstruction of images. Accordingly, the determination of the absorption profiles of the collimator 11 which are effective given various settings of the elements 13, 14 is also simplified. The determination of the absorption profiles of the collimator 11 preferably ensue for different settings of the elements 13, 14 of the collimator 11 before patient measurements. The identified absorption profiles are subsequently stored in absorption tables and can be determined from the absorption tables in the reconstruction of images from x-ray exposures produced with the computed tomography apparatus for the setting of the elements 13, 14. When, as in the case of the exemplary embodiment, the elements 13, 14 are implemented with a curvature corresponding to the circular path 16 and when they are adjustable along the circular path 16, absorption profiles need to be determined and stored only for a few settings of the elements 13, 14, since absorption profiles that prevail at settings of the elements 13, 14 other than the measured ones can be determined by simple shift operations applied to the measured absorption profiles. A shift operation means that upon a physical displacement of the elements 13, 14, a corresponding shift of the absorption values occurs to values that have been computationally determined from an absorption profile of the collimator 11 that has been previously determined and stored, the "new" values being required for the reconstruction of an image under conditions differing from the conditions for the previously determined and stored values.

Alternatively or additionally to the collimator 11, a wedge filter 20 schematically indicated in FIG. 1 can be provided for influencing the shape and/or the intensity profile of the x-rays of the x-ray source 3.

Figure 3:
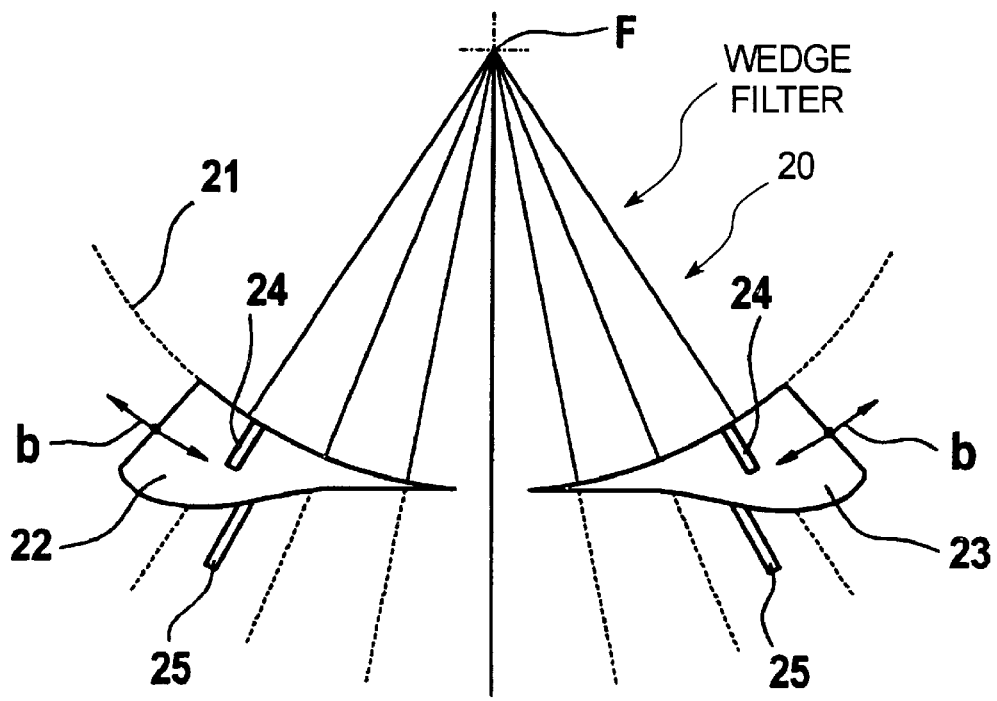
FIG. 3 shows the embodiment of a wedge filter for the computed tomography apparatus of FIG. 1.

FIG. 3 shows such a wedge filter 20 that, comparable to the collimator 11, has two elements 22, 23 that are movable in the direction of the double arrows b along the circular path 21 whose curvature center preferably lies in the focus F of the x-ray source 3. In the exemplary embodiment, the wedge filter 20 has an absorption characteristic adapted to the heart 10 under examination and is likewise adjustable with its elements 22, 23 so that the heart 10 under examination is charged with a high x-ray dose and the tissue surrounding the heart 10 is charged with a relatively low x-ray dose. Dependent on the position of the focus F relative to the heart 10, as in the case of the collimator 11, the elements 22, 23 of the wedge filter 20 are set appropriately by the collimator control 12. As in the case of the collimator 11, absorption tables are also produced for the wedge filter 20 for different settings of the elements 22, 23, usually before subject measurements, these absorption tables being utilized in the reconstruction of images of the heart 10 of the patient P.

In addition to the elements 13, 14 of the collimator 11 shown in FIG. 2 and the elements 22, 23 of the wedge filter 20 shown in FIG. 3, the collimator 11 and the wedge filter 20 also can have additional elements that are movable relative to one another and relative to the elements 13, 14, or the elements 22, 23, with which the x-ray beam can be shaped. The additional elements preferably likewise move on a circular path whose curvature center is the focus F of the x-ray source.

Fundamentally, there is the possibility of providing a number of collimators and wedge filters respectively adapted, for example, to different anatomical regions of a person on hand in the computed tomography apparatus 1 in auto-selectable fashion, and to optionally utilize these for corresponding examinations.

In order to be able to offer the absorption profile corresponding to the current setting of the collimator 11 or the wedge filter 20 to the image reconstruction system 9 for the reconstruction of images for every x-ray exposure, the computed tomography apparatus 1 in the exemplary embodiment has a measuring arrangement 17, for example distance sensors, that determine the setting of the elements 13, 14 of the collimator 11, or the setting of the elements 22, 23 of the wedge filter 20, and make this information available to the system controller 6. Alternatively, the determination of the current setting of the collimator 11 and of the wedge filter 20 can be accomplished by, as shown as an example for the wedge filter 20 in FIG. 3, structure in the form of a slot 24 and a ridge 25 that is present at each element 22, 23 of the wedge filter 20. This structure causes significant detectable changes in the intensity profiles or in the radiation attenuation profiles, identified by the x-ray detector 4 and the data measuring system 8. On the basis of the positions of the significant changes in the radiation attenuation profiles, the current setting of the collimator 11 or of the wedge filter 20 can be determined, for example on the basis of correlation algorithms and thus the appertaining absorption profiles can be identified using the absorption tables for the reconstruction of images.

These forms of determining the current settings of the collimator 11 or the wedge filter 20 in x-ray projections make mechanically complicated involved means for the exact setting of the elements 13, 14 or 22, 23 dispensable.

Nevertheless, if such mechanical means are employed for setting the elements 13, 14 of the collimator 11, or the elements 22, 23 of the wedge filter 20, and thus the precise settings of the elements 13, 14 or the elements 22, 23 are available from the control data of the collimator control 12 for each projection for the image reconstruction system 9, the measuring arrangement 17 as well as the structure that generates detectable boosts in the intensity profile can be entirely eliminated.

Various operating modes are possible for the computed tomography apparatus 1 shown in FIG. 1.

In a first operating mode, the image reconstruction system 9 provides a setting to the collimator control 12 for the size, shape and position of the radiation window 15 of the collimator 11 relative to the focus F of the x-ray source 3. The collimator control 12 correspondingly sets the elements 13, 14 of the collimator 11 according to the prescription and is setting constant during the entire registration of x-ray images.

In a second operating mode, the collimator control 12 receives measured radiation attenuation values from the data measuring system 8 via the system controller 6. The collimator control 12—during a scan—sets the size, position and shape of the radiation window 15 of the collimator 11 on the basis of radiation attenuation values measured during the course of each projection of the scan and allowing the determination of the size and of the position of the heart 10. In this mode the setting is undertaken such that the shape or the curve of the x-ray beam 7 is adapted to the position of the heart 10 of the patient P relative to the focus F of the x-ray source 3.

In a third operating mode, the image reconstruction system 9 communicates the size and the position of the heart 10 to the collimator control 12 on the basis of the identified radiation attenuation values. Additionally, the collimator control 12 receives the current rotational angle of the gantry 2 from the system controller 6, so that the collimator control 12, based on this information, can set the size, shape and position of the radiation window 12 of the collimator during the rotation of the gantry 2.

In a fourth operating mode, the setting of the shape, position and size of the radiation window 15 of the collimator 11 ensues on the basis of a function determined before the patient measurement, namely dependent on the positions to be assumed by the x-ray source 3 during the patient measurement. In the exemplary embodiment, the setting of the collimator 11 can ensue function-controlled, for example dependent on the rotational angle of the gantry 2. Such functions can be determined for the examinations of different body regions and can be applied as needed to patient measurements.

In a way analogous to the dynamic setting of the collimator 11, as was described as an example with reference to the disclosed operating modes of the computed tomography apparatus 1, the setting of the wedge filter 20 can ensue with the collimator control 12.

The wedge filter 20 can thereby be present at the x-ray apparatus and be operated alternatively to or additionally with the collimator 11. When the collimator 11 as well as the wedge filter 20 are simultaneously employed, corresponding absorption profiles that are required for the reconstruction of images must be registered at different settings at the elements of the collimator 11 and of the wedge filter 20 and must be stored for later use.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray diagnostic apparatus comprising:
   an x-ray source which emits x-rays in a beam having a shape and an intensity profile;
   an x-ray detector disposed in said beam for detecting x-rays attenuated by an examination subject disposed in said beam in a radiological exposure for producing an image of said subject; and
   a dynamically adjustable collimator disposed in said beam having a radiation window that is dynamically adjustable in size for influencing at least one of the shape and the intensity profile of said x-rays during said radiological exposure for producing said Image, said collimator having a plurality of elements that are moveable relative to each other along a circular path for dynamically adjusting said size of said window.

2. An x-ray diagnostic apparatus comprising:
   an x-ray source which emits x-rays in a beam having a shape and an intensity profile;
   an x-ray detector disposed in said beam for detecting x-rays attenuated by an examination subject disposed in said beam in a radiological exposure for producing an image of said subject: and
   a dynamically adjustable arrangement disposed in said beam for influencing at least one of the shape and the intensity profile of said x-rays during said radiological exposure for producing said image, said dynamically adjustable arrangement comprising at least one wedge filter having wedge filter elements that are movable relative to each other along a circular path.

3. An x-ray apparatus as claimed in claim 1 wherein said dynamically adjustable arrangement has a setting associated therewith which indicates said at least one of said shape and said intensity profile of said x-rays, and wherein said apparatus further comprises a measuring arrangement for identifying said setting.

4. An x-ray apparatus as claimed in claim 1 wherein said dynamically adjustable arrangement has at least one structural element which produces a detectable change in said intensity profile of said x-rays as said dynamically adjustable arrangement is adjusted.

5. An x-ray apparatus as claimed in claim 4 wherein said dynamically adjustable arrangement includes material in said beam which attenuates said x-rays, and wherein said structure comprises a portion of said material that is thinner than a remainder of said material.

6. An x-ray apparatus as claimed in claim 4 wherein said dynamically adjustable arrangement includes material in said beam which attenuates said x-rays, and wherein said structure comprises a portion of said material that is thicker than a remainder of said material.

7. A method for operating a diagnostic x-ray apparatus comprising the steps of: emitting x-rays from an x-ray source in a beam having a shape and an intensity profile;
   detecting said x-rays with an x-ray receiver after attenuation by an examination subject in a radiological exposure during which said x-ray source assumes a plurality of different positions to produce an image of said subject; and
   dynamically adjusting at least one of said shape and said intensity profile of said x-rays during said radiological exposure dependent on a function, obtained before said radiological exposure for producing said image, representing said positions of said x-ray source during said radiological exposure.

8. A method for operating a diagnostic x-ray apparatus comprising the steps of:

emitting x-rays from an x-ray source in a beam having a shape and an intensity profile;

detecting said x-rays with an x-ray receiver after attenuation by an examination subject disposed in said beam during a radiological exposure, said x-ray receiver emitting attenuation values dependent on the x-rays incident thereon during said radiological exposure to produce an image of said subject; and during said radiological exposure for producing said image, dynamically adjusting at least one of said shape and said intensity profile of said x-rays dependent on said attenuation values.

9. An x-ray apparatus as claimed in claims 2 wherein said dynamically adjustable arrangement has a setting associated therewith which indicates said at least one of said shape and said intensity profile of said x-rays, and wherein said apparatus further comprises a measuring arrangement for identifying said setting.

10. An x-ray apparatus as claimed in claim 2 wherein said dynamically adjustable arrangement has at least one structural element which produces a detectable change in said intensity profile of said x-rays as said dynamically adjustable arrangement is adjusted.

11. An x-ray apparatus as claimed in claim 10 wherein said dynamically adjustable arrangement includes material in said beam which attenuates said x-rays, and wherein said structure comprises a portion of said material that is thinner than a remainder of said material.

12. An x-ray apparatus as claimed in claim 10 wherein said dynamically adjustable arrangement includes material in said beam which attenuates said x-rays, and wherein said structure comprises a portion of said material that is thicker than a remainder of said material.

13. A method as claimed in claim 7 wherein the step of dynamically adjusting at least one of said shape and said intensity profile of said x-rays comprises moving elements which alter at least one of said shape and said intensity profile of said x-rays into said x-rays along a circular path during said radiological exposure.

14. A method as claimed in claim 8 wherein the step of dynamically adjusting at least one of said shape and said intensity profile of said x-rays comprises moving elements which alter at least one of said shape and said intensity profile of said x-rays along a circular path during said radiological exposure.

* * * * *